United States Patent
Delong et al.

(10) Patent No.: US 11,089,748 B2
(45) Date of Patent: Aug. 17, 2021

(54) SORGHUM MATERNAL HAPLOID INDUCING LINE SMHI01

(71) Applicant: PIONEER HI-BRED INTERNATIONAL, INC., Johnston, IA (US)

(72) Inventors: Rex Delong, Canyon, TX (US); Cleve Douglas Franks, Canyon, TX (US); Justin M Gifford, Lubbock, TX (US); Clifford Paul Hunter, Mililani, HI (US); Tanveer Hussain, Urbandale, IA (US); John Robert Jaster, Portland, TX (US); Maria Laura Mayor, Manhattan, KS (US); Roger Monk, Fulshear, TX (US)

(73) Assignee: PIONEER HI-BRED INTERNATIONAL, INC.

( * ) Notice: Subject to any disclaimer, the term of this patent is extended or adjusted under 35 U.S.C. 154(b) by 0 days.

(21) Appl. No.: 15/952,472

(22) Filed: Apr. 13, 2018

(65) Prior Publication Data
US 2018/0228106 A1   Aug. 16, 2018

Related U.S. Application Data

(63) Continuation of application No. PCT/US2017/064450, filed on Dec. 4, 2017.

(60) Provisional application No. 62/430,897, filed on Dec. 6, 2016.

(51) Int. Cl.
| | | |
|---|---|---|
| *A01H 5/10* | (2018.01) | |
| *A01H 1/04* | (2006.01) | |
| *A01H 6/46* | (2018.01) | |
| *A01H 1/08* | (2006.01) | |

(52) U.S. Cl.
CPC .............. *A01H 1/04* (2013.01); *A01H 1/08* (2013.01); *A01H 5/10* (2013.01); *A01H 6/4666* (2018.05)

(58) Field of Classification Search
CPC ...................................... A01H 1/04
USPC ...................................... 800/320
See application file for complete search history.

(56) References Cited

U.S. PATENT DOCUMENTS 9,043,981 B1 *  6/2015  Zorrilla .................... A01H 5/10

OTHER PUBLICATIONS

Anonymous: "Du Pont Pioneer and the sorghum checkoff collaborate to improve sorghum genetics", Apr. 14, 2014 (Apr. 14, 2014).
Anonymous: "Discovery of two haploid inducer lines in sorghum", 2017.
Dunwell, Jim M.: "Haploids in flowering plants: origins and exploitation", Plant Biotechnology Journal, May 1, 2010 (May 1, 2010), vol. 8, No. 4, pp. 377-424.
Kumaravadivel, N., et al.: "Plant regeneration from sorghum anther cultures and field evaluation of progeny", Plant Cell Reports, Feb. 1, 1994 (Feb. 1, 1994), vol. 13, No. 5.
Liang, G. H., et al.: "Haploidy in sorghum", Current Plant Science and Biotechnology in Agriculture, 1997, vol. 26, pp. 149-161.
International Search Report and Written Opinion, International Application No. PCT/US2017/064450 dated Apr. 4, 2018.

* cited by examiner

*Primary Examiner* — Li Zheng

(57) ABSTRACT

Two *Sorghum* maternal haploid inducer lines SMHI01 and SMHI02 are provided including seed, plants and plant parts thereof. Methods for producing *Sorghum* haploid embryos using SMHI01 and SMHI02 are also provided. The *Sorghum* haploid embryos produced as a result of the use of either maternal haploid inducer line SMHI01 or SMHI02 may be doubled to produce doubled haploid embryos, seeds, and plants as part of a *Sorghum* breeding program.

26 Claims, No Drawings

SORGHUM MATERNAL HAPLOID INDUCING LINE SMHI01

FIELD

The present invention relates to the field of *Sorghum* breeding and doubled haploid production.

BACKGROUND

*Sorghum, Sorghum bicolor* L., (2n=2x=20), is an important and valuable food and feed grain crop. In addition, its vegetative parts are used for forage, syrup and shelter. Thus, a continuing goal of plant breeders is to develop stable high yielding *Sorghum* hybrids that are agronomically sound. The reasons for this goal are to maximize the amount of grain produced on the land used and to supply food for both animals and humans.

However, the development of new inbred and hybrid *Sorghum* plants is slow and costly, lagging behind that of other crops such as maize. One reason is that doubled haploid breeding systems are lacking for sorghum, mainly because there are no known sorghum haploid inducer lines needed to produce sorghum haploid embryos, which is the first and foremost critical step in any doubled haploid production system.

SUMMARY

Two novel *Sorghum* haploid inducing lines SMHI01 and SMHI02, representative seed of said lines having been deposited with the ATCC on Dec. 2, 2016, are provided herein including seeds, plants, non-seed plant parts, and cells of *Sorghum* lines SMHI01 and SMHI02. The seeds, plants, non-seed plant parts, or cells of *Sorghum* lines SMHI01 and SMHI02 may comprise a marker gene that allows visual selection of haploid embryos, in which (i) the seed, non-seed plant part or cell produces a plant which has otherwise all of the phenotypic and morphological characteristics of *Sorghum* variety SMHI01 or SMHI02, or (ii) the plant has otherwise all of the phenotypic and morphological characteristics of *Sorghum* variety SMHI01 or SMHI02. The marker gene may be expressed in embryo tissue and may be expressed 4 or more days after pollination. *Sorghum* haploid embryos or plants produced by crossing a plant of SMHI01 or SMHI02 with a second plant, in which the second plant is used as a female, and *Sorghum* haploid plants produced by growing the sorghum haploid embryo or seed, are also provided.

Methods of producing *Sorghum* haploid embryos or seed are also provided in which the sorghum haploid embryos or seed are produced by pollinating a female sorghum diploid plant with pollen from *Sorghum* haploid inducer lines SMHI01 or SMHI02. The methods may further comprise selecting haploid embryos or seed based on expression of a visual marker gene.

Methods of producing *Sorghum* doubled haploid embryos, seed, or plants are also provided in which a *Sorghum* haploid embryo or seed or a *Sorghum* haploid plant, produced by pollinating female diploid plants with pollen from *Sorghum* haploid inducer lines SMHI01 or SMHI02, is placed in contact with a chromosome doubling agent. In other aspects, a *Sorghum* doubled haploid plant may be produced by growing a *Sorghum* doubled haploid embryo or seed into a *Sorghum* doubled haploid plant.

Also provided are methods for making a plant in which *Sorghum* line SMHI01 or SMHI02 is crossed to another plant. Also provided are methods for making a plant containing in its genetic material one or more traits introgressed into SMHI01 or SMHI02 through backcross conversion and/or transformation, and to the seed, plant and plant parts produced thereby. A hybrid seed, plant, or plant part produced by crossing line SMHI01 or SMHI02, or a locus conversion of SMHI01 or SMHI02, with another plant is also provided.

DETAILED DESCRIPTION

Definitions

In the description and examples that follow, a number of terms are used herein. In order to provide a clear and consistent understanding of the specification and claims, including the scope to be given such terms, the following definitions are provided:

A haploid plant has a single set (genome) of chromosomes and the reduced number of chromosomes (n) in the haploid plant is equal to that in the gamete (for *Sorghum bicolor*, n=10).

A diploid plant has two sets (genomes) of chromosomes and the chromosome number (2n) is equal to that in the zygote (for *Sorghum bicolor*, 2n=20).

A doubled haploid or doubled haploid plant or cell is one that is developed by the doubling of a haploid set of chromosomes. A plant or seed that is obtained from a doubled haploid plant that is selfed any number of generations may still be identified as a doubled haploid plant. A doubled haploid plant is considered a homozygous plant. A plant is considered to be doubled haploid if it is fertile, even if the entire vegetative part of the plant does not consist of the cells with the doubled set of chromosomes. For example, a plant will be considered a doubled haploid plant if it contains viable gametes, even if it is chimeric.

A "haploid immature embryo" is defined as the embryo formed after one sperm nucleus from a pollen grain fuses with the polar nuclei in the embryo sac to create a triploid (3N) endosperm and before dry down.

A "doubled haploid embryo" is an embryo that has one or more cells that contain 2 sets of homozygous chromosomes.

The phrases "contacting", "comes in contact with" or "placed in contact with" can be used to mean "direct contact" or "indirect contact". For example, the medium comprising a chromosome doubling agent may have direct contact with the haploid cell or the medium comprising the chromosome doubling agent may be separated from the haploid cell by filter paper, plant tissues, or other cells thus the chromosome doubling agent is transferred through the filter paper or cells to the haploid cell.

As used herein, the term "plant" includes reference to whole plants, plant organs (e.g., leaves, stems, roots, etc.), seeds and plant cells and progeny of same. "Plant cell", as used herein includes, without limitation, seeds, suspension cultures, embryos, meristematic regions, callus tissue, leaves, roots, shoots, gametophytes, sporophytes, pollen, and microspores. The class of plants which can be used in the methods of provided include both monocotyledonous and dicotyledonous plants.

Anthracnose Resistance. This is a visual rating based on the number of lesions caused by anthracnose infection. A score of 9 would indicate little necrosis and a score of 1 would indicate plant death as a result of anthracnose infection.

Bacterial Spot. Bacterial Spot is a disease characterized by small, irregularly shaped lesions on the leaves. Bacterial Spot Resistance is rated on a scale of 1 to 9, with 1 being susceptible and 9 being resistant.

Bacterial Streak. Bacterial Streak is a disease characterized by narrow yellow stripes on the leaves. Bacterial Streak Resistance is rated on a scale of 1 to 9, with 1 being susceptible and 9 being resistant.

Bacterial Stripe. Bacterial Stripe is a disease characterized by long, narrow red stripes on the leaves. Bacterial Stripe Resistance is rated on a scale of 1 to 9, with 1 being susceptible and 9 being resistant.

Biotype C Greenbug Resistance. This is a visual rating based on the amount of necrosis on leaves and stems caused by biotype C greenbug feeding. A score of 9 would indicate no leaf or stem damage as a result of greenbug feeding.

Biotype E Greenbug Resistance. This is a visual rating based on plant seedlings ability to continue growing when infested with large numbers of biotype E greenbugs. A score of 9 indicates normal growth and a score of 1 indicates seedling death.

Charcoal Rot. Charcoal Rot is a disease characterized by rotting of the roots and stalks. Charcoal Rot Resistance is rated on a scale of 1 to 9, with 1 being susceptible and 9 being resistant.

Chinch Bug Resistance. This is a visual rating based on the plants ability to grow normally when infested with large numbers of chinch bugs. A score of 9 would indicate normal growth and a score of 1 would indicate severe plant stunting and death.

Crop Response to Herbicide. Rated as the visual difference between sprayed and un-sprayed plants. A crop response of less than 30% means no visual difference, higher percentages means sprayed plants showed some damage.

Days to Color. The days to color is the number of days required for an inbred line or hybrid to begin grain coloring from the time of planting. Coloring of the grain is correlated with physiological maturity, thus days to color gives an estimate of the period required before a hybrid is ready for harvest.

Days to Flower. The days to flower is the number of days required for an inbred line or hybrid to shed pollen from the time of planting.

Downy Mildew Resistance (Pathotypes 1, 3, and 6). This is a visual rating based on the percentage of downy mildew infected plants. A score of 9 indicates no infected plants. A score of 1 would indicate higher than 50% infected plants. Ratings are made for infection by each pathotype of the disease.

Drought Tolerance. This represents a rating for drought tolerance and is based on data obtained under stress. It is based on such factors as yield, plant health, lodging resistance and stay green. A high score would indicate a hybrid tolerant to drought stress.

Dry Down. This represents the relative rate at which a plant will reach acceptable harvest moisture compared to other plants. A high score indicates a plant that dries relatively fast while a low score indicates a plant that dries slowly.

*Fusarium* Root and Stalk Rot. *Fusarium* Root and Stalk Rot is a disease characterized by rotting of the roots and stalks. *Fusarium* Root and Stalk Rot Resistance is rated on a scale of 1 to 9, with 1 being susceptible and 9 being resistant.

Grain Mold. Grain Mold is characterized by the formation of mold on heads and grain. Grain Mold Resistance is rated on a scale of 1 to 9, with 1 being susceptible and 9 being resistant.

Gray Leaf Spot Resistance. This is a visual rating based on the number of gray leaf spot lesions present on the leaves and stem of the plant. A score of 9 would indicate the presence of few lesions.

Head Exertion. This represents a rating for the length of the peduncle exposed between the base of the panicle (head) and the flag leaf of the plant. A high score indicates more distance between the flag leaf and the *Sorghum* head while a low score indicates a short distance between the two. Head exertion facilitates ease of combine harvesting.

Head Smut Resistance (Races 1-5). This is a visual rating based on the percentage of smut infected plants. A score of 9 would indicate no infected plants and a score of 1 would indicate higher than 50% infected plants. Ratings are made for each race of head smut.

Head Type. This represents a rating of the morphology of the *Sorghum* panicle (head). A high score indicates an open panicle caused by either more distance between panicle branches or longer panicle branches. A low score indicates a more compact panicle caused by shorter panicle branches arranged more closely on the central rachis.

Leaf Burn Resistance. This is a visual rating based on the amount of tissue damage caused by exposure to insecticide sprays. A score of 9 would indicate minor leaf spotting and a score of 1 would indicate leaf death as a result of contact with insecticide spray.

Locus Conversion (Also called a Trait Conversion): A locus conversion refers to a modified plant within a variety that retains the overall genetics of the variety and further includes a locus with one or more specific desired traits, and otherwise has the same, essentially the same, all or essentially all of the physiological and morphological characteristics of the variety, such as listed in Table 1. Traits can be directed to, for example, modified grain, male sterility, insect control, disease control or herbicide tolerance. Traits can be mutant genes, transgenic sequences or native traits. A single locus conversion refers to plants within a variety that have been modified in a manner that retains the overall genetics of the variety and include a single locus with one or more specific desired traits. A single locus conversion can include at least or about 1, 2, 3, 4 or 5 traits and less than or about 15, 10, 9, 8, 7 or 6 traits. A locus converted plant can include, for example, at least or about 1, 2 or 3 and less than or about 20, 15, 10, 9, 8, 7, 6, or 5 modified loci while still retaining the overall genetics of the variety and otherwise having essentially the same, the same, all or essentially all of the physiological and morphological characteristics of the variety, such as listed in Table 1. The total number of traits at one or more locus conversions can be, for example, at least or about 1, 2, 3, 4 or 5 and less than or about 25, 20, 15, 10, 9, 8, 7 or 6. Examples of single locus conversions include mutant genes, transgenes and native traits finely mapped to a single locus. Traits may be introduced by transformation, backcrossing, or a combination of both.

Maize Dwarf Mosaic Virus Resistance. This is a visual rating based on the percentage of plants showing symptoms of virus infection. A score of 9 would indicate no plants with virus symptoms and a 1 would indicate a high percentage of plants showing symptoms of virus infection such as stunting, red leaf symptoms or leaf mottling.

Midge Resistance. This is a visual rating based on the percentage of seed set in the panicle in the presence of large numbers of midge adults. A score of 9 would indicate near normal seed set and a score of 1 would indicate no seed set in the head due to midge damage.

Moisture. The moisture is the actual percentage moisture of the grain at harvest.

Percent Yield. The percent yield is the yield obtained from the hybrid in terms of percent of the mean for the experiment in which it was grown.

Plant: As used herein, the term "plant" includes reference to an immature or mature whole plant, including a plant from which seed or grain has been removed.

Plant Height. This is a measure of the average height of the hybrid from the ground to the tip of the panicle and is measured in inches.

Plant Part: As used herein, the term "plant part" includes leaves, stems, roots, seed, grain, kernels, panicles, embryo, pollen, ovules, flowers, stalks, root tips, anthers, pericarp, protoplasts, tissue, plant calli, cells and the like. In some embodiments the plant part contains at least one cell of hybrid *Sorghum* variety SMHI01 AND SMHI02.

Predicted RM. This trait, predicted relative maturity (RM), for a hybrid is based on the number of days required for an inbred line or hybrid to shed pollen from the time of planting. The relative maturity rating is based on a known set of checks and utilizes standard linear regression analyses.

*Puccinia* (Rust) Resistance. This is a visual rating based on the number of rust pustules present on the leaves and stem of the plant. A score of 9 would indicate the presence of few rust pustules.

RM to Color. This trait for a hybrid is based on the number of days required for a hybrid to begin to show color development in the grain from the time of planting. The relative maturity rating is based on a known set of checks and utilizes standard linear regression analyses.

Root Lodging. This represents a rating of the percentage of plants that do not root lodge, i.e. those that lean from the vertical axis at an approximate 30 degree angle or greater without stalk breakage are considered to be root lodged. This is a relative rating of a hybrid to other hybrids for standability. Root lodging is rated on a scale of 1 to 9, with 1 indicating greater than 50% lodged plants and 9 indicating no lodged plants.

Sales Appearance. This represents a rating of the acceptability of the hybrid in the market place. It is a complex score including such factors as hybrid uniformity, appearance of yield, grain texture, grain color and general plant health. A high score indicates the hybrid would be readily accepted based on appearance only. A low score indicates hybrid acceptability to be marginal based on appearance only.

Salt Tolerance. This represents a rating of the plants ability to grow normally in soils having high sodium salt content. This is a relative rating of a hybrid to other hybrids for normal growth.

Selection Index. The selection index gives a single measure of the hybrid's worth based on information for up to five traits. A *Sorghum* breeder may utilize his or her own set of traits for the selection index. Two of the traits that are almost always included are yield and days to flower (maturity). The selection index data presented in the tables in the specification represent the mean values averaged across testing stations.

Sooty Stripe. Sooty Stripe is a disease characterized by elongate, elliptical lesions on the leaves. Sooty Stripe Resistance is rated on a scale of 1 to 9, with 1 being susceptible and 9 being resistant.

Stalk Lodging. This represents a rating of the percentage of plants that do not stalk lodge, i.e. stalk breakage above the ground caused by natural causes. This is a relative rating of a hybrid to other hybrids for standability. Stalk lodging is rated on a scale of 1 to 9, with 1 indicating greater than 50% lodged plants and 9 indicating no lodged plants.

Stay Green. Stay green is the measure of plant health near the time of harvest. A high score indicates better late-season plant health.

Test Weight. This is the measure of the weight of the grain in pounds for a given volume (bushel) adjusted for percent moisture.

Weathering. This represents a rating of how well the exposed grains are able to retain normal seed quality when exposed to normal weather hazards and surface grain molds.

Yield (cwt/acre). The yield in cwt/acre is the actual yield of the grain at harvest adjusted to 13% moisture.

Yield/RM. This represents a rating of a hybrid yield compared to other hybrids of similar maturity or RM. A high score would indicate a hybrid with higher yield than other hybrids of the same maturity.

Yield Under Stress. This is a rating of the plants ability to produce grain under heat and drought stress conditions. A score of 9 would indicate near normal growth and grain yield and a score of 1 would indicate substantial yield reduction due to stress.

Zonate Leaf Spot Resistance. This is a visual rating based on the number of zonate leaf spot lesions present on the leaves and stem of the plant. A score of 9 would indicate the presence of few lesions.

Two maternal haploid inducing lines SMHI01 and SMHI02 have been discovered in *Sorghum* (*Sorghum bicolor*). To validate their utility as maternal haploid inducers, *Sorghum* female plants were hand-pollinated with pollen from the newly discovered haploid inducing lines, and at plant maturity, seeds were harvested from the female plants. The F1 harvested seed was then planted to screen for putative haploid plants. Haploid plants were validated via chromosome counting, flow cytometry, and phenotypic analysis.

Compositions

The two novel *Sorghum* haploid inducing lines SMHI01 and SMHI02, representative seed of said lines having been deposited with the ATCC on Dec. 2, 2016, are provided herein including seeds, plants, non-seed plant parts, and cells of *Sorghum* lines SMHI01 and SMHI02.

The seeds, plants, non-seed plant parts, or cells of *Sorghum* lines SMHI01 and SMHI02 may comprise a marker gene that allows visual selection of haploid embryos, in which (i) the seed, non-seed plant part or cell produces a plant which has otherwise all of the phenotypic and morphological characteristics of *Sorghum* variety SMHI01 or SMHI02, or (ii) the plant has otherwise all of the phenotypic and morphological characteristics of *Sorghum* variety SMHI01 or SMHI02. The visible marker gene may be, for example, a colored marker such as GUS (U.S. Pat. Nos. 5,599,670 and 5,432,081), GFP (U.S. Pat. Nos. 6,146,826; 5,491,084; and WO 97/41228), luciferase (U.S. Pat. No. 5,674,713 and Ow et al. 1986 *Science* 234 (4778) 856-859), YFP, CFP, CRC (Ludwig et al., 1990 *Science* 247(4841): 449-450), coral reef proteins, anthocyanin genes such as A, C, R-nj, R1-scm alleles, R1-mb (marbled aleurone), R1-r: standard, R1-Randolph, R1-ch:Stadler, R1-d:Catspaw, R1-d:Arapaho, R1-nj, R1-nj:Cudu, R1-nj:Chase, R1-scm2, R1-sc:124, R1-sup-R1-suppressible, R1 K10-11; R1 r1-X1, R1-ch, R1-g, R1-1sk, R1-r, R1-sc122, R1-sc*5691, R1-sc: m122, R1-sc:m2, R1-scm:3, R1-sk:nc-2, R1-sk, R1-st, or any other known to one of ordinary skill in the art.

For various reasons it may be desirable to express the marker gene in the embryo. In particular, it may be desirable to express the marker gene in the early stage of development, about 10 hours-15 days after pollination. Thus, in some aspects, the marker gene may be expressed in embryo tissue at 4 or more days after pollination. If the marker is a transgene, using an appropriate promoter such as an oleosin or a Lec1 promoter may be beneficial. Haploid embryos can then be distinguished from the normally pollinated embryos because the haploid embryos will not contain the marker gene. The markers may be come through the female or male plant. The preferable method is to have the markers come through the male plant.

*Sorghum* haploid embryos, seeds, or plants produced by crossing a plant of SMHI01 or SMHI02 with a second plant, in which the second plant is used as a female, and *Sorghum* haploid plants produced by growing the *Sorghum* haploid embryo or seed, are also provided.

Methods of Use Relating to Haploid Induction

Also provided are methods for 1) producing *Sorghum* haploid embryos or seed, 2) producing *Sorghum* doubled haploid embryos, seed, or plants by contacting *Sorghum* haploid embryos, seed, or plants with a chromosome doubling agent, and 3) producing *Sorghum* doubled haploid plants by contacting *Sorghum* haploid embryos or seed with a chromosome doubling agent and growing the *Sorghum* doubled haploid embryos or seed into *Sorghum* doubled haploid plants.

To generate *Sorghum* haploid embryos, seeds, or plants, pollen from either SMHI01 or SMHI02 can be used to pollinate the stigmas of *Sorghum* diploid plants. Prior to pollination, the *Sorghum* plants that are to be used as females may be emasculated using any known emasculation technique. For example, part of the peduncle may be emasculated by clipping off florets that are about to flower; a *Sorghum* head may be immersed in hot water (typically 45-48° C. for a period of about 10 minutes; or *Sorghum* heads may be covered with a plastic bag to create high humidity inside the bag, thereby inhibiting pollen shed. Alternatively, the female plants may have a cytoplasmic male sterility trait. The stigmas of the female parent *Sorghum* plants may then be pollinated with viable pollen grains collected from the anthers of SMHI01 or SMHI02. Pollination may be performed using a paint brush in a controlled environment; the collected pollen may be dusted over exposed stigma; or the pollen producing head (from the haploid male inducer line) may be brushed over an emasculated head. Identification of *Sorghum* haploid embryos may be aided by the use of a marker gene as described above.

*Sorghum* haploid cells, haploid embryos, haploid seeds, haploid seedlings or haploid plants can be treated with a chromosome doubling agent. Homozygous plants can be regenerated from haploid cells by contacting the haploid cells, such as haploid embryo cells, with chromosome doubling agents. The haploid cells may come in contact with the chromosome doubling agent at the time of pollination, anytime after pollination, typically 6 hours to 21 days after pollination, 6 hours to 15 days after pollination, at the mature seed stage, at the seedling stage, or at the plant stage. The haploid embryo may come in contact with the chromosome doubling agent when one sperm nucleus from a pollen grain fuses with the polar nuclei in the embryo sac to create a triploid (3N) endosperm (when the haploid embryo is formed), anytime after the pollination, typically 6 hours to 21 days after pollination, 6 hours to 15 days after pollination, or at the mature seed stage. The haploid embryo may be isolated. It may be contained within the kernel, ovule, or seed. It may also be on the panicle in the case of *Sorghum*. The panicle comprising the haploid embryo may be on the plant or isolated from the plant. The panicle also may be sectioned. After chromosome doubling, the doubled haploid embryo will contain 2 copies of maternally derived chromosomes.

Methods of chromosome doubling are disclosed in Antoine-Michard, S. et al., *Plant cell, tissue organ cult.*, Cordrecht, the Netherlands, Kluwer Academic Publishers, 1997, 48(3):203-207; Kato, A., *Maize Genetics Cooperation Newsletter* 1997, 36-37; and Wan, Y. et al., *TAG*, 1989, 77: 889-892. Wan, Y. et al., *TAG*, 1991, 81: 205-211, the disclosures of which are incorporated herein by reference. Typical methods involve contacting the cells with colchicine, anti-microtubule agents or anti-microtubule herbicides, pronamide, nitrous oxide, or any mitotic inhibitor to create homozygous doubled haploid cells. The amount of colchicine used in medium is generally 0.01%-0.2% or approximately 0.05% or APM (5-225 µM). The amount of colchicines can range from approximately 400-600 mg/L or approximately 500 mg/L. The amount of pronamide in medium is approximately 0.5-20 µM. Other agents may be used with the mitotic inhibitors to improve doubling efficiency. Such agents may be dimethyl sulfoxide (DMSO), adjuvants, surfactants, and the like.

The duration of contact between the chromosomal doubling agent may vary. Contact may be from less than 24 hours, for example 4-12 hours, to about a week. The duration of contact is generally from about 24 hours to 2 days.

Methods for obtaining homozygous plants, plant cells, and seeds are provided herein.

One method comprises obtaining a *Sorghum* doubled haploid embryo, seed, or plant by contacting a *Sorghum* haploid embryo, produced by pollinating stigmas of a *Sorghum* female diploid plant with SMHI01 or SMHI02, with a chromosome doubling agent and obtaining a doubled haploid embryo, seed, or plant.

In another method, *Sorghum* doubled haploid plants are obtained using a method comprising the following steps: a) pollinating stigmas of a *Sorghum* diploid plant with pollen from inducer line SMHI01 or SMHI02, wherein the inducer line has a marker gene that is expressed in embryos and/or endosperm tissue; b) selecting a *Sorghum* haploid embryo which does not express a marker gene; c) contacting the *Sorghum* haploid embryo with a gas, solution or solid comprising a chromosome doubling agent; and d) regenerating the resulting *Sorghum* doubled haploid embryo into a doubled haploid plant.

In another method, *Sorghum* doubled haploid seed is obtained using a method comprising the following steps: a) obtaining a *Sorghum* haploid seed by pollinating an ovule with inducer line SMHI01 or SMHI02 wherein the ovule comprises a set of maternal chromosomes and wherein the inducer line comprises a set of paternal chromosomes; b) contacting the *Sorghum* haploid seed with a medium comprising a chromosome doubling agent; c) selecting a *Sorghum* doubled haploid seed wherein the *Sorghum* doubled haploid seed comprises a triploid endosperm and a doubled haploid embryo. The *Sorghum* doubled haploid seed produced by such a method wherein the triploid endosperm comprises two sets of maternal chromosomes and one set of paternal chromosomes, and wherein the *Sorghum* doubled haploid embryo has a first and second set of maternal chromosomes and wherein the first set of maternal chromosomes is homozygous to the second set of maternal chromosomes can be produced. Also included is a method of determining the origin of the chromosomes with the use of a marker that is expressed during early seed development.

In another method, a population of doubled haploid *Sorghum* plants is obtained using a method comprising the following steps: a) obtaining a set of *Sorghum* haploid kernels by pollinating stigmas of a panicle with inducer line SMHI01 or SMHI02, wherein the panicle comprises a set of maternal chromosomes and wherein the inducer line comprises a set of paternal chromosomes; b) contacting said set of *Sorghum* haploid kernels with a medium comprising a chromosome doubling agent; c) selecting a set of *Sorghum* doubled haploid kernels wherein each kernel of said set of *Sorghum* doubled haploid kernels comprises a triploid endosperm and a doubled haploid embryo; d) growing said set of *Sorghum* doubled haploid kernels into a population of doubled haploid *Sorghum* plants. The set of *Sorghum* doubled haploid kernels produced have triploid endosperm and the triploid endosperm comprises two sets of maternal chromosomes and one set of paternal chromosomes. The doubled haploid embryo also has two sets of maternal chromosomes. These two sets of chromosomes are homozygous. The first set of chromosomes being replicated to form the second set of chromosomes. The various sets obtained from these methods can include the set of embryos on a *Sorghum* panicle, the set of kernels on a *Sorghum* panicle, and the set of *Sorghum* doubled haploids plants.

In another method, a doubled haploid *Sorghum* plant is obtained using a method comprising: a) pollinating stigmas of a *Sorghum* panicle with inducer line SMHI01 or SMHI02; b) contacting the *Sorghum* panicle with a medium comprising a chromosome doubling agent; c) generating an embryo from the *Sorghum* panicle into a doubled haploid *Sorghum* plant. Other aspects of the method include removing the *Sorghum* panicle from the plant with or without the stalk or some portion of the stalk attached. The panicle can be removed before, during, or after pollination and placed into a solution. The panicle can be placed in a solution 6 hours to 21 days after pollination and up to 35 days after pollination. The solution may comprise water or water and nutrients. The solution may come into contact with the panicle directly or indirectly, for example via filter paper or cotton. The chromosome doubling agent can come in contact with the panicle after pollination and before or after the panicle is removed from the plant. The chromosomal doubling agent may come into contact with the panicle directly or indirectly, for example via filter paper or cotton.

In another method, a set of doubled haploid *Sorghum* embryos is obtained using a method comprising the following steps: a) obtaining a set of *Sorghum* haploid embryos by pollinating a panicle with pollen from inducer line SMHI01 or SMHI02; wherein the panicle comprises a set of maternal chromosomes from an F1 *Sorghum* plant; and wherein the inducer line comprises a set of paternal chromosomes; b) contacting said set of *Sorghum* haploid embryos with a medium comprising a chromosome doubling agent; c) selecting a set of doubled haploid *Sorghum* embryos wherein each doubled haploid *Sorghum* embryo of said set of doubled haploid *Sorghum* embryos is genetically different from each of the other doubled haploid *Sorghum* embryos of said set of doubled haploid *Sorghum* embryos; d) growing said set of doubled haploid *Sorghum* embryos into a population of doubled haploid *Sorghum* plants. This method develops a unique set of doubled haploid *Sorghum* embryos. This unique set of embryos is derived directly from one *Sorghum* panicle, wherein "being derived directly" indicates that a filial generation does not occur between development of the haploid embryos and the development of the set of doubled haploid embryos.

A method of inbred selection is also provided in which the method comprises the following steps: a) cross pollinating two inbred *Sorghum* plants; b) growing the F1 seed; c) pollinating the F1 plant with inducer line SMHI01 or SMHI02 to produce *Sorghum* haploid embryos; d) contacting the *Sorghum* haploid embryos with a chromosome doubling agent to produce *Sorghum* doubled haploid embryos; e) generating *Sorghum* doubled haploid plants; f) evaluating said *Sorghum* doubled haploid plants for agronomic performance and combining ability. The development of haploids step may also be done at later generations, F2, F3, F4, etc. Producing haploids from later generations allows for additional opportunities for recombination.

Breeding with SMHI01 or SMHI02

Field crops are bred through techniques that take advantage of the plant's method of pollination. A plant is self-pollinating if pollen from one flower is transferred to the same or another flower of the same plant. A plant is cross-pollinated if the pollen comes from a flower on a different plant.

Plants that have been self-pollinated and selected for type for many generations become homozygous at almost all gene loci and produce a uniform population of true breeding progeny. A cross between two homozygous plants from differing backgrounds or two homozygous lines produce a uniform population of hybrid plants that may be heterozygous for many gene loci. A cross of two plants that are each heterozygous at a number of gene loci will produce a population of hybrid plants that differ genetically and will not be uniform.

*Sorghum* plants (*Sorghum bicolor* L. Moench) are bred in most cases by self-pollination techniques. With the incorporation of male sterility (either genetic or cytoplasmic) cross pollination breeding techniques can also be utilized. *Sorghum* has a perfect flower with both male and female parts in the same flower located in the panicle. The flowers are usually in pairs on the panicle branches. Natural pollination occurs in *Sorghum* when anthers (male flowers) open and pollen falls onto receptive stigma (female flowers). Because of the close proximity of male (anthers) and female (stigma) in the panicle, self-pollination is very high (average 94%). Cross pollination may occur when wind or convection currents move pollen from the anthers of one plant to receptive stigma on another plant. Cross pollination is greatly enhanced with incorporation of male sterility which renders male flowers nonviable without affecting the female flowers. Successful pollination in the case of male sterile flowers requires cross pollination.

*Sorghum* is in the same family as maize and has a similar growth habit, but with more tillers and a more extensively branched root system. *Sorghum* is more drought resistant and heat-tolerant than maize. It requires an average temperature of at least 25° C. to produce maximum yields. *Sorghum*'s ability to thrive with less water than maize may be due to its ability to hold water in its foliage better than maize. *Sorghum* has a waxy coating on its leaves and stems which helps to keep water in the plant even in intense heat. Wild species of *Sorghum* tend to grow to a height of 1.5 to 2 meters; however in order to improve harvestability, dwarfing genes have been selected in cultivated varieties and hybrids such that most cultivated varieties and hybrids grow to between 60 and 120 cm tall.

Inbred Development

The development of *Sorghum* hybrids requires the development of homozygous inbred lines, the crossing of these lines, and the evaluation of the crosses. Pedigree breeding methods, and to a lesser extent population breeding methods, are used to develop inbred lines from breeding populations. Breeding programs combine desirable traits from two or more inbred lines into breeding pools from which new inbred lines are developed by selfing and selection of desired phenotypes. The new inbreds are crossed with other inbred lines and the hybrids from these crosses are evaluated to determine which have commercial potential.

Pedigree breeding starts with the crossing of two genotypes, each of which may have one or more desirable characteristics that is lacking in the other or which complement the other. If the two original parents do not provide all of the desired characteristics, other sources can be included in the breeding population. In the pedigree method, superior plants are selfed and selected in successive generations. In the succeeding generations the heterozygous condition gives way to homogeneous lines as a result of self-pollination and selection. Typically, in the pedigree method of breeding five or more generations of selfing and selection is practiced. $F_1$ to $F_2$; $F_2$ to $F_3$; $F_3$ to $F_4$, $F_4$ to $F_5$, etc.

Backcrossing can be used to improve an inbred line. Backcrossing transfers a specific desirable trait from one inbred or source to an inbred that lacks that trait. This can be accomplished for example by first crossing a superior inbred (A) (recurrent parent) to a donor inbred (non-recurrent parent), which carries the appropriate genes(s) for the trait in question. The progeny of this cross is then mated back to the superior recurrent parent (A) followed by selection in the resultant progeny for the desired trait to be transferred from the non-recurrent parent. After five or more backcross generations with selection for the desired trait, the progeny will be heterozygous for loci controlling the characteristic being transferred, but will be like the superior parent for most or almost all other genes. The last backcross generation would be selfed to give pure breeding progeny for the gene(s) being transferred.

Controlling Self-Pollination

Sorghum varieties are mainly self-pollinated; therefore, self-pollination of the parental varieties must be controlled to make hybrid development feasible. A pollination control system and effective transfer of pollen from one parent to the other offers improved plant breeding and an effective method for producing hybrid seed and plants. For example, the milo or $A_1$ cytoplasmic male sterility (CMS) system, developed via a cross between milo and kafir cultivars, is one of the most frequently used CMS systems in hybrid Sorghum production (Stephens J C & Holland P F, Cytoplasmic Male Sterility for Hybrid Sorghum Seed Production, Agron. J. 46:20-23 (1954)). Other CMS systems for Sorghum include, but are not limited to, $A_2$, isolated from IS 12662c (Schertz K F, Registration of $A_2T_x$ 2753 and $BT_x$ 2753 Sorghum Germplasm, Crop Sci. 17: 983 (1977)), $A_3$, isolated from IS 1112c or converted Nilwa (Quinby J R, Interactions of Genes and Cytoplasms in Male-Sterility in Sorghums, Proc. 35th Corn Sorghum Res. Conf. Am. Seed Trade Assoc. Chicago, Ill., pp. 5-8 (1980)), $A_4$, isolated from IS 7920c (Worstell et al, Relationship among Male-Sterility Inducing Cytoplasms of Sorghum, Crop Sci. 24:186-189 (1984)).

In developing improved new Sorghum hybrid varieties, breeders may use a CMS plant as the female parent. In using these plants, breeders attempt to improve the efficiency of seed production and the quality of the $F_1$ hybrids and to reduce the breeding costs. When hybridization is conducted without using CMS plants, it is more difficult to obtain and isolate the desired traits in the progeny ($F_1$ generation) because the parents are capable of undergoing both cross-pollination and self-pollination. If one of the parents is a CMS plant that is incapable of producing pollen, only cross pollination will occur. By eliminating the pollen of one parental variety in a cross, a plant breeder is assured of obtaining hybrid seed of uniform quality, provided that the parents are of uniform quality and the breeder conducts a single cross.

In one instance, production of $F_1$ hybrids includes crossing a CMS female parent with a pollen-producing male parent. To reproduce effectively, however, the male parent of the $F_1$ hybrid must have a fertility restorer gene (Rf gene). The presence of an Rf gene means that the $F_1$ generation will not be completely or partially sterile, so that either self-pollination or cross pollination may occur. Self-pollination of the $F_1$ generation to produce several subsequent generations is important to ensure that a desired trait is heritable and stable and that a new variety has been isolated.

Promising advanced breeding lines commonly are tested and compared to appropriate standards in environments representative of the commercial target area(s). The best lines are candidates for new commercial lines; and those still deficient in a few traits may be used as parents to produce new populations for further selection.

Hybrid Development

A hybrid Sorghum variety is the cross of two inbred lines, each of which may have one or more desirable characteristics lacked by the other or which complement the other. The hybrid progeny of the first generation is designated $F_1$. In the development of hybrids only the $F_1$ hybrid plants are sought. The $F_1$ hybrid is more vigorous than its inbred parents. This hybrid vigor, or heterosis, can be manifested in many ways, including increased vegetative growth and increased yield.

The development of a hybrid Sorghum variety involves five steps: (1) the formation of "restorer" and "non-restorer" germplasm pools; (2) the selection of superior plants from various "restorer" and "non-restorer" germplasm pools; (3) the selfing of the superior plants for several generations to produce a series of inbred lines, which although different from each other, each breed true and are highly uniform; (4) the conversion of inbred lines classified as non-restorers to cytoplasmic male sterile (CMS) forms, and (5) crossing the selected cytoplasmic male sterile (CMS) inbred lines with selected fertile inbred lines (restorer lines) to produce the hybrid progeny ($F_1$).

Because Sorghum is normally a self-pollinated plant and because both male and female flowers are in the same panicle, large numbers of hybrid seed can only be produced by using cytoplasmic male sterile (CMS) inbreds. Flowers of the CMS inbred are fertilized with pollen from a male fertile inbred carrying genes which restore male fertility in the hybrid ($F_1$) plants. An important consequence of the homozygosity and homogeneity of the inbred lines is that the hybrid between any two inbreds will always be the same. Once the inbreds that produce the best hybrid have been identified, the hybrid seed can be reproduced indefinitely as long as the homogeneity of the inbred parent is maintained.

A single cross hybrid is produced when two inbred lines are crossed to produce the $F_1$ progeny. Much of the hybrid vigor exhibited by $F_1$ hybrids is lost in the next generation ($F_2$). Consequently, seed from hybrid varieties is not used for planting stock.

Hybrid grain Sorghum can be produced using wind to move the pollen. Alternating strips of the cytoplasmic male sterile inbred (female) and the male fertile inbred (male) are planted in the same field. Wind moves the pollen shed by the male inbred to receptive stigma on the female. Providing that there is sufficient isolation from sources of foreign Sorghum pollen, the stigma of the male sterile inbred (female) will be fertilized only with pollen from the male fertile inbred (male). The resulting seed, born on the male sterile (female) plants is therefore hybrid and will form hybrid plants that have full fertility restored.

Locus Conversions of *Sorghum* Line SMHI01 AND SMHI02

SMHI01 and SMHI02 represent new base genetic lines into which a new locus or trait may be introduced. Direct transformation and backcrossing represent two important methods that can be used to accomplish such an introgression. The term locus conversion is used to designate the product of such an introgression.

To select and develop a superior hybrid, it is necessary to identify and select genetically unique individuals that occur in a segregating population. The segregating population is the result of a combination of crossover events plus the independent assortment of specific combinations of alleles at many gene loci that results in specific and unique genotypes. Once such a variety is developed its value to society is substantial since it is important to advance the germplasm base as a whole in order to maintain or improve traits such as yield, disease resistance, pest resistance and plant performance in extreme weather conditions. Locus conversions are routinely used to add or modify one or a few traits of such a line and this further enhances its value and usefulness to society.

Backcrossing can be used to improve inbred varieties and a hybrid variety which is made using those inbreds. Backcrossing can be used to transfer a specific desirable trait from one variety, the donor parent, to an inbred called the recurrent parent which has overall good agronomic characteristics yet that lacks the desirable trait. This transfer of the desirable trait into an inbred with overall good agronomic characteristics can be accomplished by first crossing a recurrent parent to a donor parent (non-recurrent parent). The progeny of this cross is then mated back to the recurrent parent followed by selection in the resultant progeny for the desired trait to be transferred from the non-recurrent parent.

Traits may be used by those of ordinary skill in the art to characterize progeny. Traits are commonly evaluated at a significance level, such as a 1%, 5% or 10% significance level, when measured in plants grown in the same environmental conditions. For example, a locus conversion of SMHI01 or SMHI02 may be characterized as having essentially the same phenotypic traits as SMHI01 or SMHI02. Molecular markers can also be used during the breeding process for the selection of qualitative traits. For example, markers can be used to select plants that contain the alleles of interest during a backcrossing breeding program. The markers can also be used to select for the genome of the recurrent parent and against the genome of the donor parent. Using this procedure can minimize the amount of genome from the donor parent that remains in the selected plants.

A locus conversion of SMHI01 or SMHI02 will retain the genetic integrity of SMHI01 or SMHI02. A locus conversion of SMHI01 or SMHI02 will comprise at least 92%, 93%, 94%, 95%, 96%, 97%, 98% or 99% of the base genetics of SMHI01 or SMHI02. For example, a locus conversion of SMHI01 or SMHI02 can be developed when DNA sequences are introduced through backcrossing (Hallauer et al., 1988), with a parent of SMHI01 or SMHI02 utilized as the recurrent parent. Both naturally occurring and transgenic DNA sequences may be introduced through backcrossing techniques. A backcross conversion may produce a plant with a locus conversion in at least one or more backcrosses, including at least 2 crosses, at least 3 crosses, at least 4 crosses, at least 5 crosses and the like. Molecular marker assisted breeding or selection may be utilized to reduce the number of backcrosses necessary to achieve the backcross conversion. For example, see Openshaw, S. J. et al., Marker-assisted Selection in Backcross Breeding. In: Proceedings Symposium of the Analysis of Molecular Data, August 1994, Crop Science Society of America, Corvallis, Oreg., where it is demonstrated that a backcross conversion can be made in as few as two backcrosses. A locus conversion of SMHI01 AND SMHI02 can be determined through the use of a molecular profile. A locus conversion of SMHI01 AND SMHI02 would have 92%, 93%, 94%, 95%, 96%, 97%, 98% or 99% of the molecular markers, or molecular profile, of SMHI01 or SMHI02. Examples of molecular markers that could be used to determine the molecular profile include Restriction Fragment Length Polymorphisms (RFLP), Polymerase Chain Reaction (PCR) analysis, and Simple Sequence Repeats (SSR), and Single Nucleotide Polymorphisms (SNPs).

Transformation of *Sorghum* Line SMHI01 or SMHI02

The advent of new molecular biological techniques has allowed the isolation and characterization of genetic elements with specific functions, such as encoding specific protein products. Scientists in the field of plant biology developed a strong interest in engineering the genome of plants to contain and express foreign genetic elements, or additional, or modified versions of native or endogenous genetic elements in order to alter the traits of a plant in a specific manner. Any DNA sequences, whether from a different species or from the same species, that are inserted into the genome using transformation are referred to herein collectively as "transgenes."

Numerous methods for plant transformation have been developed, including biological and physical plant transformation protocols. See, for example, Miki, et al., "Procedures for Introducing Foreign DNA into Plants" in Methods in Plant Molecular Biology and Biotechnology, Glick. In addition, expression vectors and in vitro culture methods for plant cell or tissue transformation and regeneration of plants are available. See, for example, Gruber, et al., "Vectors for Plant Transformation" in Methods in Plant Molecular Biology and Biotechnology, Glick and Thompson, Eds. (CRC Press, Inc., Boca Raton, 1993) pages 89-119.

The most prevalent types of plant transformation involve the construction of an expression vector. Such a vector comprises a DNA sequence that contains a gene under the control of or operatively linked to a regulatory element, for example a promoter. The vector may contain one or more genes and one or more regulatory elements.

A genetic trait which has been engineered into a particular *Sorghum* plant using transformation techniques, could be moved into another line using traditional breeding techniques that are well known in the plant breeding arts. For example, a backcrossing approach could be used to move a transgene from a transformed *Sorghum* plant to an elite inbred line and the resulting progeny would comprise a transgene. Also, if an inbred line was used for the transformation then the transgenic plants could be crossed to a different line in order to produce a transgenic hybrid *Sorghum* plant. As used herein, "crossing" can refer to a simple X by Y cross, or the process of backcrossing, depending on the context. Various genetic elements can be introduced into the plant genome using transformation. These elements include but are not limited to genes; coding sequences; inducible, constitutive, and tissue specific promoters; enhancing sequences; and signal and targeting sequences. For example, see, U.S. Pat. No. 6,118,055.

With transgenic plants according to the present discovery, a foreign protein can be produced in commercial quantities. Thus, techniques for the selection and propagation of transformed plants, which are well understood in the art, yield a plurality of transgenic plants which are harvested in a conventional manner, and a foreign protein then can be extracted from a tissue of interest or from total biomass. Protein extraction from plant biomass can be accomplished by known methods which are discussed, for example, by Heney and Orr, (1981) Anal. Biochem. 114:92-96.

A genetic map can be generated, primarily via conventional Restriction Fragment Length Polymorphisms (RFLP), Polymerase Chain Reaction (PCR) analysis, and Simple Sequence Repeats (SSR), and Single Nucleotide Polymorphisms (SNPs), which identifies the approximate chromosomal location of the integrated DNA molecule coding for the foreign protein. For exemplary methodologies in this regard, see, Glick and Thompson, METHODS IN PLANT MOLECULAR BIOLOGY AND BIOTECHNOLOGY 269-284 (CRC Press, Boca Raton, 1993). Map information concerning chromosomal location is useful for proprietary protection of a subject transgenic plant. If unauthorized propagation is undertaken and crosses made with other germplasm, the map of the integration region can be compared to similar maps for suspect plants, to determine if the latter have a common parentage with the subject plant. Map comparisons would involve hybridizations, RFLP, PCR, SSR, SNP, and sequencing, all of which are conventional techniques.

Likewise, by means of the present discovery, plants can be genetically engineered to express various phenotypes of agronomic interest. Exemplary transgenes implicated in this regard include, but are not limited to, those categorized below.

1. Genes that Create a Site for Site Specific DNA Integration.

This includes the introduction of FRT sites that may be used in the FLP/FRT system and/or Lox sites that may be used in the Cre/Loxp system. For example, see, Lyznik, et al., (2003) "Site-Specific Recombination for Genetic Engineering in Plants", *Plant Cell Rep* 21:925-932 and WO 99/25821, which are hereby incorporated by reference. Other systems that may be used include the Gin recombinase of phage Mu (Maeser, et al., 1991), the Pin recombinase of *E. coli* (Enomoto, et al., 1983), and the R/RS system of the pSR1 plasmid (Araki, et al., 1992).

2. Genes that affect abiotic stress resistance (including but not limited to flowering, panicle/glume and seed development, enhancement of nitrogen utilization efficiency, altered nitrogen responsiveness, drought resistance or tolerance, cold resistance or tolerance, and salt resistance or tolerance) and increased yield under stress.

For example, see, WO 00/73475 where water use efficiency is altered through alteration of malate; U.S. Pat. Nos. 5,892,009, 5,965,705, 5,929,305, 5,891,859, 6,417,428, 6,664,446, 6,706,866, 6,717,034, 6,801,104, WO2000060089, WO2001026459, WO2001035725, WO2001034726, WO2001035727, WO2001036444, WO2001036597, WO2001036598, WO2002015675, WO2002017430, WO2002077185, WO2002079403, WO2003013227, WO2003013228, WO2003014327, WO2004031349, WO2004076638, WO9809521 and WO9938977 describing genes, including CBF genes and transcription factors effective in mitigating the negative effects of freezing, high salinity, and drought on plants, as well as conferring other positive effects on plant phenotype; US Patent Application Publication Number 2004/0148654 and WO01/36596 where abscisic acid is altered in plants resulting in improved plant phenotype such as increased yield and/or increased tolerance to abiotic stress; WO2000/006341, WO04/090143, U.S. patent application Ser. Nos. 10/817,483 and 09/545,334 where cytokinin expression is modified resulting in plants with increased stress tolerance, such as drought tolerance, and/or increased yield. Also see WO0202776, WO03052063, JP2002281975, U.S. Pat. No. 6,084,153, WO0164898, U.S. Pat. Nos. 6,177,275 and 6,107,547 (enhancement of nitrogen utilization and altered nitrogen responsiveness). For ethylene alteration, see, US Patent Application Publication Numbers 2004/0128719, 2003/0166197 and WO200032761. For plant transcription factors or transcriptional regulators of abiotic stress, see e.g., US Patent Application Publication Number 2004/0098764 or US Patent Application Publication Number 2004/0078852.

Other genes and transcription factors that affect plant growth and agronomic traits such as yield, flowering, plant growth and/or plant structure, can be introduced or introgressed into plants, see, e.g., WO97/49811 (LHY), WO98/56918 (ESD4), WO97/10339 and U.S. Pat. No. 6,573,430 (TFL), U.S. Pat. No. 6,713,663 (FT), WO96/14414 (CON), WO96/38560, WO01/21822 (VRN1), WO00/44918 (VRN2), WO99/49064 (GI), WO00/46358 (FRI), WO97/29123, U.S. Pat. Nos. 6,794,560, 6,307,126 (GAI), WO99/09174 (D8 and Rht), and WO2004076638 and WO2004031349 (transcription factors).

3. Transgenes that confer or contribute to an altered grain characteristic, such as:
   A. Altered phosphorus content, for example, by the
   (1) Introduction of a phytase-encoding gene would enhance breakdown of phytate, adding more free phosphate to the transformed plant. For example, see, Van Hartingsveldt, et al., Gene 127:87 (1993), for a disclosure of the nucleotide sequence of an *Aspergillus niger* phytase gene.
   (2) Up-regulation of a gene that reduces phytate content. In maize, this, for example, could be accomplished, by cloning and then re-introducing DNA associated with one or more of the alleles, such as the LPA alleles, identified in maize mutants characterized by low levels of phytic acid, such as in Raboy, et al. (1990).
   B. Altered fatty acids, for example, by down-regulation of stearoyl-ACP desaturase to increase stearic acid content of the plant. See Knultzon, et al., Proc. Natl. Acad. Sci. USA 89:2624 (1992).
   C. Altered carbohydrates effected, for example, by altering a gene for an enzyme that affects the branching pattern of starch, a gene altering thioredoxin. (See, U.S. Pat. No. 6,531,648). See, Shiroza, et al., (1988) J. Bacteriol 170:810 (nucleotide sequence of *Streptococcus mutans* fructosyltransferase gene), Steinmetz, et al., (1985) Mol. Gen. Genet. 200:220 (nucleotide sequence of *Bacillus subtilis* levansucrase gene), Pen, et al., (1992) Bio/Technology 10:292 (production of transgenic plants that express *Bacillus licheniformis* alpha-amylase), Elliot, et al., (1993) Plant Molec Biol 21:515 (nucleotide sequences of tomato invertase genes), Søgaard, et al., (1993) J. Biol. Chem. 268:22480 (site-directed mutagenesis of barley alpha-amylase gene) and Fisher, et al., (1993) Plant Physiol 102:1045 (maize endosperm starch branching enzyme II), WO 99/10498 (improved digestibility and/or starch extraction through modification of UDP-D-xylose 4-epimerase, Fragile 1 and 2, Ref1, HCHL, C4H), U.S. Pat. No. 6,232,529 (method of producing high oil seed by modification of starch levels (AGP)). The fatty acid modification genes mentioned above may also be used to affect starch content and/or composition through the interrelationship of the starch and oil pathways.

D. Altered antioxidant content or composition, such as alteration of tocopherol or tocotrienols. For example, see, U.S. Pat. No. 6,787,683, US Patent Application Publication Number 2004/0034886 and WO 00/68393 involving the manipulation of antioxidant levels through alteration of a phytl prenyl transferase (ppt), WO 03/082899 through alteration of a homogentisate geranyl geranyl transferase (hggt).

E. Altered essential seed amino acids. For example, see, U.S. Pat. No. 6,127,600 (method of increasing accumulation of essential amino acids in seeds), U.S. Pat. No. 6,080,913 (binary methods of increasing accumulation of essential amino acids in seeds), U.S. Pat. No. 5,990,389 (high lysine), WO99/40209 (alteration of amino acid compositions in seeds), WO99/29882 (methods for altering amino acid content of proteins), U.S. Pat. No. 5,850,016 (alteration of amino acid compositions in seeds), WO98/20133 (proteins with enhanced levels of essential amino acids), U.S. Pat. No. 5,885,802 (high methionine), U.S. Pat. No. 5,885,801 (high threonine), U.S. Pat. No. 6,664,445 (plant amino acid biosynthetic enzymes), U.S. Pat. No. 6,459,019 (increased lysine and threonine), U.S. Pat. No. 6,441,274 (plant tryptophan synthase beta subunit), U.S. Pat. No. 6,346,403 (methionine metabolic enzymes), U.S. Pat. No. 5,939,599 (high sulfur), U.S. Pat. No. 5,912,414 (increased methionine), WO98/56935 (plant amino acid biosynthetic enzymes), WO98/45458 (engineered seed protein having higher percentage of essential amino acids), WO98/42831 (increased lysine), U.S. Pat. No. 5,633,436 (increasing sulfur amino acid content), U.S. Pat. No. 5,559,223 (synthetic storage proteins with defined structure containing programmable levels of essential amino acids for improvement of the nutritional value of plants), WO96/01905 (increased threonine), WO95/15392 (increased lysine), US Patent Application Publication Number 2003/0163838, US Patent Application Publication Number 2003/0150014, US Patent Application Publication Number 2004/0068767, U.S. Pat. No. 6,803,498, WO01/79516, and WO00/09706 (Ces A: cellulose synthase), U.S. Pat. No. 6,194,638 (hemicellulose), U.S. Pat. No. 6,399,859 and US Patent Application Publication Number 2004/0025203 (UDPGdH), U.S. Pat. No. 6,194,638 (RGP).

4. Genes that Confer Male Sterility

There are several methods of conferring genetic male sterility available, such as multiple mutant genes at separate locations within the genome that confer male sterility, as disclosed in U.S. Pat. Nos. 4,654,465 and 4,727,219 to Brar, et al., and chromosomal translocations as described by Patterson in U.S. Pat. Nos. 3,861,709 and 3,710,511. In addition to these methods, Albertsen, et al., U.S. Pat. No. 5,432,068, describes a system of nuclear male sterility which includes: identifying a gene which is critical to male fertility; silencing this native gene which is critical to male fertility; removing the native promoter from the essential male fertility gene and replacing it with an inducible promoter; inserting this genetically engineered gene back into the plant; and thus creating a plant that is male sterile because the inducible promoter is not "on" resulting in the male fertility gene not being transcribed. Fertility is restored by inducing, or turning "on," the promoter, which in turn allows the gene that confers male fertility to be transcribed.

A. A dominant nuclear gene, Ms(tc) controlling male sterility. See, Elkonin, L. A., *Theor. Appl. Genet.* (2005) 111(7): 1377-1384.

B. A tapetum-specific gene, RTS, a *Sorghum* anther-specific gene is required for male fertility and its promoter sequence directs tissue-specific gene expression in different plant species. Luo, Hong, et al., Plant Molecular Biology., 62(3): 397-408(12) (2006). Introduction of a deacetylase gene under the control of a tapetum-specific promoter and with the application of the chemical N-Ac-PPT. See International Publication No. WO 01/29237.

C. Introduction of various stamen-specific promoters. Anther-specific promoters which are of particular utility in the production of transgenic male-sterile monocots and plants for restoring their fertility. See, U.S. Pat. No. 5,639,948. See also, International Publication Nos. WO 92/13956 and WO 92/13957.

D. Introduction of the barnase and the barstar genes. See, Paul, et al., *Plant Mol. Biol.*, 19:611-622 (1992).

For additional examples of nuclear male and female sterility systems and genes, see also, U.S. Pat. Nos. 5,859,341, 6,297,426, 5,478,369, 5,824,524, 5,850,014, and 6,265,640. See also, Hanson, Maureen R., et al., "Interactions of Mitochondrial and Nuclear Genes That Affect Male Gametophyte Development," *Plant Cell.*, 16:S154-S169 (2004), all of which are hereby incorporated by reference.

A. Modification of RNA editing within mitochondrial open reading frames. See, Pring, D. R., et al, *Curr. Genet.* (1998) 33(6): 429-436; Pring, D. R., et al., *J. Hered.* (1999) 90(3): 386-393; Pring, D. R., et al., *Curr. Genet.* (2001) 39(5-6): 371-376; and Hedgcoth, C., et al., *Curr. Genet.* (2002) 41(5): 357-365.

B. Cytoplasmic male sterility (CMS) from mutations at atp6 codons. See, Kempken, F., *FEBS. Lett.* (1998): 441(2): 159-160.

C. Inducing male sterility through heat shock. See, Wang, L., *Yi Chuan Xue Bao.* (2000) 27(9): 834-838.

D. Inducing male sterility through treatment of streptomycin on *Sorghum* callus cultures. See, Elkonin, L. A., et al., *Genetica* (2008) 44(5): 663-673.

Uses of *Sorghum*

*Sorghum* is used as livestock feed, as sugar or grain for human consumption, as biomass, and as raw material in industry. *Sorghum* grain can be used as livestock feed, such as to beef cattle, dairy cattle, hogs and poultry. In some embodiments, the plant is used as livestock feed in the form of fodder, silage, hay and pasture. In some embodiments, commodity plant products produced from hybrid seed such as food, feed, forage, and syrup are provided.

Provided are uses of *Sorghum* in the form of bread, porridge, confectionaries and as an alcoholic beverage. Grain *Sorghum* may be ground into flour and either used directly or blended with wheat or corn flour in the preparation of food products. In addition to direct consumption of the grain, *Sorghum* has long been used in many areas of the world to make beer. The uses of *Sorghum*, in addition to human consumption of kernels, include both products of dry and wet milling industries. The principal products of *Sorghum* dry milling are grits, meal and flour. Starch and other extracts for food use can be provided by the wet milling process.

Also provided are uses of *Sorghum* as an industrial raw material. Industrial uses include *Sorghum* starch from the wet-milling industry and *Sorghum* flour from the dry milling industry. *Sorghum* starch and flour have application in the paper and textile industries. Other industrial uses include applications in adhesives, building materials and as oil-well muds. Considerable amounts of *Sorghum*, both grain and plant material, have been used in industrial alcohol production.

Provided are seed of *Sorghum* lines SMHI01 and SMHI02, plants of *Sorghum* lines SMHI01 and SMHI02, plant parts of *Sorghum* lines SMHI01 and SMHI02, and processes for making a plant that comprise crossing *Sorghum* line SMHI01 or SMHI02 with another plant. In some embodiments, SMHI01 or SMHI02 may be provided with cytoplasm comprising a gene or genes that cause male sterility. Also disclosed are processes for making a plant containing in its genetic material one or more traits introgressed into SMHI01 or SMHI02 through backcross conversion and/or transformation, and to the seed, plant and plant arts produced thereby. Hybrid *Sorghum* seed, plant, or plant part produced by crossing line SMHI01 or SMHI02 or a locus conversion of SMHI01 or SMHI02 with another plant are also provided.

The terms variants, modification and mutant refer to a hybrid seed or a plant produced by that hybrid seed which is phenotypically similar to SMHI01 or SMHI02.

All publications and patent applications mentioned in this specification are herein incorporated by reference to the same extent as if each individual publication or patent application was specifically and individually indicated to be incorporated by reference.

EXAMPLES

The present disclosure is further illustrated in the following Examples, in which parts and percentages are by weight and degrees are Celsius, unless otherwise stated. It should be understood that these Examples, while indicating embodiments of the disclosure, are given by way of illustration only. From the above discussion and these Examples, one skilled in the art can ascertain the essential characteristics of this disclosure, and without departing from the spirit and scope thereof, can make various changes and modifications of the disclosure to adapt it to various usages and conditions. Thus, various modifications of the disclosure in addition to those shown and described herein will be apparent to those skilled in the art from the foregoing description. Such modifications are also intended to fall within the scope of the appended claims.

Example 1

Screening for Haploid Inducer Lines

Screening of proprietary and public *Sorghum* lines was performed to identify potential haploid inducers. Two *Sorghum* lines produced haploid plants (Table 1) when per se inbred seed was planted, indicating that SMHI01 and SMHI02 are haploid inducers.

TABLE 1

Identification of SMHI01 and SMHI02 as haploid inducers

| Genotype | # seed germinated | # diploid plants | % diploid plants | # Haploid plants | % Haploid plants |
|---|---|---|---|---|---|
| SMHI01 | 196 | 193 | 98.5% | 3 | 1.5% |
| SMHI02 | 165 | 164 | 99.4% | 1 | 0.6% |

Example 2

Obtaining Haploid Plants by Pollination with New Inducer Line SMHI01

A maternal-haploid-inducing *Sorghum* line named SMHI01 was used to pollinate 6 different female inbred plants "A", "B", "C", "D", "E", and "F". The head or panicles of the female parent plants were given hot water treatment before the start of anthesis to sterilize the panicles and avoid self-pollination. Panicles of the female plants were pollinated with pollen collected from the head of the haploid inducer line. Seed was harvested when panicles were mature. Panicles harvested from the female plant contained seeds with haploid and diploid embryos. Harvested seed was planted as head-to-row in the field. In a second set of experiments, plants from diploid *Sorghum* genotypes "D", "E", and "F" were pollinated with pollen obtained from haploid inducer line SMHI01; and the hybrid cross seed was harvested and planted as head-to-row in another location.

The plant stand count was collected on germinated seedling as the number of seed germinated. At flowering, phenotypic data such as plant stature, leaf type, plant height, panicle filled or unfilled, days to flowering, and flowering pattern were collected. Leaf samples were taken to test the ploidy level using a flow cytometer. Based on flow cytometry results and plant phenotype, the putative haploid plants were examined and confirmed as true haploid plants. Table 2 shows the percentage of haploid plants generated from each F1 cross using SMHI01 as the pollinator.

TABLE 2

Results from field evaluations with parent SMHI01

| Genotype | # seed germinated | # diploid plants | % diploid plants | # Haploid plants | % Haploid plants |
|---|---|---|---|---|---|
| A/SMHI01* | 244 | 240 | 98.4% | 4 | 1.6% |
| B/SMHI01 | 183 | 180 | 98.4% | 3 | 1.6% |
| C/SMHI01 | 35 | 32 | 91.4% | 3 | 8.6% |
| D/SMHI01* | 371 | 368 | 99.2% | 3 | 0.8% |
| E/SMHI01 | 180 | 179 | 99.4% | 1 | 0.6% |
| F/SMHI01 | 195 | 193 | 99.0% | 2 | 1.0% |
| Sum (for hybrid crosses) | 1208 | 1192 | 98.7% | 16 | 1.3% |

*Plants arising from hybrid cross D/SMHI01 were evaluated in two locations, while plants arising from hybrid cross A/SMHI01 were evaluated over two years.

The different female genotypes were used in order to evaluate the effect with different female backgrounds. The results indicate that each female line exhibits a varying degree of haploid frequencies when crossed with haploid inducer line SMHI01.

Example 3

Obtaining Haploid Plants by Pollination with New Inducer Line SMHI02

A maternal-haploid-inducing *Sorghum* line named SMHI02 was used to pollinate female inbred "A". The head or panicles of the female parent plants were given hot water treatment before the start of anthesis to sterilize the panicles and avoid self-pollination. Panicles of the female plants were pollinated with pollen collected from the head of the haploid inducer line. Seed was harvested when panicles were mature. Panicles harvested from the female plant contained seeds with haploid and diploid embryos. Harvested seed was planted as head-to-row in the field.

The plant stand count was collected on germinated seedling as the number of seed germinated. At flowering, phenotypic data such as plant stature, leaf type, plant height, panicle filled or unfilled, days to flowering, and flowering pattern were collected. Leaf samples were taken to test the ploidy level using a flow cytometer. Based on flow cytometry results and plant phenotype, the putative haploid plants were examined and confirmed as true haploid plants. Table 3 shows the percentage of haploid plants generated from the F1 cross using SMHI02 as the pollinator.

TABLE 3

Results from field evaluations with parent SMHI02

| Genotype | # seed germinated | # diploid plants | % diploid plants | # Haploid plants | % Haploid plants |
|---|---|---|---|---|---|
| A/SMHI02 | 137 | 135 | 98.4% | 2 | 1.5% |

Example 4

Obtaining Chromosome Counts from Root Tips of Putative *Sorghum* Haploid Plants Through Cytological Techniques To confirm the ploidy level of the putative haploid plants, cytological techniques were used on the hybrid seed generated from the crossing of female *Sorghum* lines with SMHI01. Root tips of the plants were taken into the laboratory for preparation of root squash. Fresh root tips (~1 inch) from the plant were immersed in acetic:alcohol (3:1) for 10 minutes and were washed before immersing them in acetocarmine solution for 10 minutes for staining purposes. The root tips were then placed on a microscope slide and the debris and other tissue was cleared away with a sharp scalpel. By pushing the root tips with the back of the scalpel, the internal cells were expelled on the slide. At the end, a cover slip was placed over the root tip cell and excess fluid was removed. Chromosomes were detected and counted in the root tip cells using an inverted compound microscope.

Example 5

Testing the Ploidy Level of Putative Haploid Plants Using Flow Cytometry

To verify the ploidy level of putative haploid plants, leaf samples were taken from each plant, and each plant sample was tested using a standard flow cytometry protocol. Leaf samples of diploid plants were used as controls. Flow cytometry clearly distinguished haploid plants from diploid plants; thus, the putative haploid inducing lines SMHI01 and SMHI02 were confirmed as inducer lines.

Example 6

Obtaining Phenotypes from Putative Haploid and Diploid *Sorghum* Plants

To verify the ploidy level of putative haploid seeds, the seeds produced from each of plant are planted as head-to-row in the field. The plants within each head-to-row are evaluated for their phenotypes at flowering, such as, plant height, plant shape, plant panicle shape, number of spikelets per spike, flowering time, and seed set at maturity (Table 4). Haploid plants are sterile and don't shed pollen 5 and thus do not produce selfed seed. However, normal diploid plants are fertile, shed pollen at flowering, and produce selfed seed at maturity.

TABLE 4

| Variety Name | SMHI01 |
|---|---|
| Kind | Sorghum |
| Male Sterile Cytoplasm | R |
| Use Class: | Grain |
| Days from planting to mid-anthesis | 66 |
| Plant Coleptile | Green |
| Plant pigment | Red |
| Plant: Natural height of foliage at panicle emergence | Medium |
| Plant: Total height at maturity | Medium |
| Diameter of main stalk | Mid stout |
| Waxy Bloom | present |
| Number of Tillers | Medium |
| Stem Sweetness | insipid |
| Panicle Exsertion | Short |
| Degree of Senescence | intermediate |
| Leaf Color | Dark green |
| Leaf: Width of blade of first leaf below flag leaf | Narrow |
| Leaf margin | Wavy |
| Leaf attitude or erectness | Horizontal |
| Ligule | Present |
| Leaf midrib color (first leaf below flag leaf) | intermediate |
| Panicle Anther Color (at flowering) | light yellow |
| Panicle Density | Compact |
| Panicle Shape at maturity | Cylindrical |
| Length of central rachis (% of panicle length) | 100% |
| Panicle erectness | Erect |
| Rachis branches at grain maturity | Erect |
| Rachis Branch Average | intermediate |
| Panicle Type | More cylindrical sorghum panicle type |
| Rachis branches | heavily fruited |
| Heads break at maturity | No |
| Glume length at maturity | Long |
| Percent of grain covered by the glume | 50% |
| Glume Texture | intermediate |
| Glume color at grain maturity | Dark Tan |
| Glume Hairiness or pubescence | Hairy |
| Glume Veination | Absent |
| Glume Transverse Wrinkle | Absent |
| Glume Awns | Absent |
| Roots | Fibrous |
| Grain Testa | Absent |
| Grain Mesocarp Thickness | intermediate |
| Grain Epicarp Color (Genetic) | Yellow |
| Grain Spreader (Tannin in Pericarp) | Absent |
| Grain Intensifier | Absent |
| Grain Color (Appearance) | Light Red |
| Grain Endosperm Color | white |
| Grain Endosperm Type | Starchy |
| Grain Endosperm Texture | intermediate |
| Grain Seed Shape | round |
| No. of seed per 100 G Genotype | 3852 |

DEPOSITS

Applicant has made a deposit of at least 2500 seeds of *Sorghum* Line SMHI01 with the American Type Culture Collection (ATCC), 10801 University Boulevard, Manassas, Va. 20110-2209, USA. The seeds deposited with the ATCC on Dec. 2, 2016 as PTA-123711 were obtained from the seed of the variety maintained by Pioneer Hi-Bred International, Inc., 7250 NW 62nd Avenue, Johnston, Iowa, 50131 since prior to the filing date of this application. Access to this seed will be available during the pendency of the application to the Commissioner of Patents and Trademarks and persons determined by the Commissioner to be entitled thereto upon request. Upon allowance of any claims in the application, the Applicant will make the deposit available to the public pursuant to 37 C.F.R. § 1.808. This deposit of the *Sorghum* Line SMHI01 will be maintained in the ATCC depository, which is a public depository, for a period of 30 years, or 5 years after the most recent request, or for the enforceable life of the patent, whichever is longer, and will be replaced if it becomes nonviable during that period. Additionally, Applicant has or will satisfy all of the requirements of 37 C.F.R. §§ 1.801-1.809, including providing an indication of the viability of the sample upon deposit. Applicant has no authority to waive any restrictions imposed by law on the transfer of biological material or its transportation in commerce. Applicant does not waive any infringement of rights granted under this patent or under the Plant Variety Protection Act (7 USC 2321 et seq.).

Applicant has also made a deposit of at least 2500 seeds of *Sorghum* Line SMHI02 with the American Type Culture Collection (ATCC), 10801 University Boulevard, Manassas, Va. 20110-2209, USA. The seeds deposited with the ATCC on Dec. 2, 2016 were obtained from the seed of the variety maintained by Pioneer Hi-Bred International, Inc., 7250 NW 62nd Avenue, Johnston, Iowa, 50131 since prior to the filing date of this application. Access to this seed will be available during the pendency of the application to the Commissioner of Patents and Trademarks and persons determined by the Commissioner to be entitled thereto upon request. Upon allowance of any claims in the application, the Applicant will make the deposit available to the public pursuant to 37 C.F.R. § 1.808. This deposit of the *Sorghum* Line SMHI02 will be maintained in the ATCC depository, which is a public depository, for a period of 30 years, or 5 years after the most recent request, or for the enforceable life of the patent, whichever is longer, and will be replaced if it becomes nonviable during that period. Additionally, Applicant has or will satisfy all of the requirements of 37 C.F.R. §§ 1.801-1.809, including providing an indication of the viability of the sample upon deposit. Applicant has no authority to waive any restrictions imposed by law on the transfer of biological material or its transportation in commerce. Applicant does not waive any infringement of rights granted under this patent or under the Plant Variety Protection Act (7 USC 2321 et seq.).

What is claimed is:

1. A plant, non-seed plant part, seed, or cell of sorghum variety SMHI01, representative seed of said line having been deposited with the ATCC as PTA-123711.

2. The plant, non-seed plant part, seed, or cell of claim 1, further comprising a marker gene that allows visual selection of haploid embryos, wherein (i) the seed, non-seed plant part or cell produces a plant which has otherwise all of the phenotypic and morphological characteristics of sorghum variety SMHI01, or (ii) the plant has otherwise all of the phenotypic and morphological characteristics of sorghum variety SMHI01.

3. The plant, non-seed plant part, seed, or cell of claim 2, wherein the marker gene is expressed in embryo tissue.

4. The plant, non-seed plant part, seed, or cell of claim 2, wherein the marker gene is expressed 4 or more days after pollination.

5. An F1 sorghum haploid embryo or seed produced by crossing the plant of claim 1 with a second plant, wherein said second plant is used as a female.

6. A sorghum haploid plant produced by growing the sorghum haploid embryo or seed of claim 5.

7. A method of producing a sorghum haploid embryo or seed, said method comprising pollinating a female sorghum diploid plant with pollen from sorghum haploid inducer line SMHI01, representative seed of said line having been deposited with the ATCC as PTA-123711, wherein said pollination results in production of a sorghum haploid embryo or seed.

8. The method of claim 7, further comprising selecting haploid embryos based on expression of a visual marker gene.

9. A method of producing a sorghum doubled haploid embryo, seed, or plant, said method comprising contacting the sorghum haploid embryo or seed of claim 5 or the sorghum haploid plant of claim 6 with a chromosome doubling agent.

10. A method of producing a sorghum doubled haploid plant, said method comprising contacting the sorghum haploid embryo or seed of claim 5 with a chromosome doubling agent and growing the sorghum doubled haploid embryo or seed into a sorghum doubled haploid plant.

11. An F1 sorghum seed or a plant grown therefrom, the seed produced by crossing the plant or non-seed plant part of claim 2 with a different plant.

12. A plant part of the F1 sorghum seed or plant of claim 11, wherein the plant part comprises at least one cell of the F1 sorghum seed or plant.

13. The plant, non-seed plant part, seed or plant cell of claim 2, further comprising a locus conversion, wherein the plant or a plant grown from the plant part, seed or plant cell otherwise comprises all of the physiological and morphological characteristics of sorghum variety SMHI01 when grown under the same environmental conditions.

14. The plant, non-seed plant part, seed, or plant cell of claim 4, wherein the locus conversion confers a property selected from the group consisting of abiotic stress tolerance, altered phosphate content, altered antioxidant content, altered fatty acid profile, altered essential amino acid profile, altered carbohydrate content, herbicide resistance, insect resistance, disease resistance, and salt tolerance.

15. A method for generating a haploid inducing line, the method comprising crossing the seed, plant or non-seed plant part of claim 2 with another different plant to produce progeny seed and selecting a haploid inducing line from the progeny seed.

16. A method for generating a haploid inducing line, the method comprising crossing the seed or plant of claim 11 with another different plant to produce progeny seed and selecting a haploid inducing line from the progeny seed.

17. A plant, non-seed plant part, seed, or plant cell of sorghum variety SMHI01, representative seed of the variety having been deposited under ATCC accession number PTA-123711, the plant, non-seed plant part, seed, or plant cell further comprising a single locus conversion, wherein the single locus conversion is introduced into sorghum variety SMHI01 by backcrossing or transformation.

18. The plant, plant part, seed, or plant cell of claim 17, wherein the locus conversion confers a property selected from the group consisting of abiotic stress tolerance, altered phosphate content, altered antioxidant content, altered fatty acid profile, altered essential amino acid profile, altered carbohydrate content, herbicide resistance, insect resistance, disease resistance, and salt tolerance.

19. A sorghum seed produced by crossing the plant or non-seed plant part of claim 1 with a different plant.

20. An F1 plant produced by growing the seed of claim 19.

21. A plant part comprising at least one cell of the F1 plant of claim 20.

22. A method of producing a sorghum seed, the method comprising crossing two sorghum plants and harvesting the resultant sorghum seed, wherein at least one of the sorghum plants is the sorghum plant of claim 1.

23. A method of producing a sorghum seed, the method comprising crossing two sorghum plants and harvesting the resultant sorghum seed, wherein at least one of the sorghum plants is the sorghum plant of claim 2.

24. A method of producing a sorghum seed, the method comprising crossing two sorghum plants and harvesting the resultant sorghum seed, wherein at least one of the sorghum plants is the sorghum plant of claim 3.

25. A method of producing a sorghum seed, the method comprising crossing two sorghum plants and harvesting the resultant sorghum seed, wherein at least one of the sorghum plants is the sorghum plant of claim 6.

26. A method of plant breeding, the method comprising: (a) crossing a plant of sorghum variety SMHI01 with a second plant comprising a desired single locus to produce F1 progeny plants, representative seed of said sorghum variety SMHI01 having been deposited under ATCC Accession No. PTA-123711; and (b) selecting at least a first progeny plant from step (a) that comprises the single locus to produce a selected progeny plant.

\* \* \* \* \*